(12) United States Patent
Nahrwold et al.

(10) Patent No.: US 10,369,093 B2
(45) Date of Patent: Aug. 6, 2019

(54) STABLE SOLUTION OF HEXAMIDINE SALTS IN ALKANEDIOL-WATER MIXTURES, WITH ANTIMICROBIAL AND SKIN-MOISTURISING EFFECT

(71) Applicant: MINASOLVE GERMANY GMBH, Leuna (DE)

(72) Inventors: Markus Nahrwold, Minden (DE); Nadia Konaté, Magdeburg (DE)

(73) Assignee: Minasolve Germany GmbH, Leuna (DE)

( * ) Notice: Subject to any disclaimer, the term of this patent is extended or adjusted under 35 U.S.C. 154(b) by 0 days.

(21) Appl. No.: 15/765,990

(22) PCT Filed: Sep. 30, 2016

(86) PCT No.: PCT/EP2016/073475
§ 371 (c)(1),
(2) Date: Apr. 4, 2018

(87) PCT Pub. No.: WO2017/060173
PCT Pub. Date: Apr. 13, 2017

(65) Prior Publication Data
US 2018/0280268 A1     Oct. 4, 2018

(30) Foreign Application Priority Data

Oct. 5, 2015   (DE) ........................ 10 2015 116 835

(51) Int. Cl.
| | | |
|---|---|---|
| *A61K 8/04* | (2006.01) |
| *A61K 8/06* | (2006.01) |
| *A61K 8/33* | (2006.01) |
| *A61K 8/34* | (2006.01) |
| *A61K 8/42* | (2006.01) |
| *A61Q 17/00* | (2006.01) |
| *A61Q 19/00* | (2006.01) |
| *A61Q 19/10* | (2006.01) |

(52) U.S. Cl.
CPC ................ *A61K 8/42* (2013.01); *A61K 8/042* (2013.01); *A61K 8/062* (2013.01); *A61K 8/33* (2013.01); *A61K 8/345* (2013.01); *A61Q 17/005* (2013.01); *A61Q 19/007* (2013.01); *A61Q 19/10* (2013.01); *A61K 2800/10* (2013.01)

(58) Field of Classification Search
None
See application file for complete search history.

(56) References Cited

U.S. PATENT DOCUMENTS 7,582,681 B2 * 9/2009 Schmaus ................ A01N 31/02
424/44

FOREIGN PATENT DOCUMENTS

| DE | 20221386 U1 | 10/2005 |
| EP | 1477157 A1 | 11/2004 |
| EP | 1779839 A1 | 5/2007 |
| WO | WO 2012170695 A2 | 12/2012 |

OTHER PUBLICATIONS

International Search Report received in PCT Application No. PCT/EP2016/073475, dated Dec. 20, 2016.

* cited by examiner

*Primary Examiner* — Brian J Davis
(74) *Attorney, Agent, or Firm* — Knobbe, Martens, Olson & Bear, LLP

(57) ABSTRACT

The invention relates to a temperature-stable solution consisting of
a) 0.1-10% by weight of at least one hexamidine salt,
b) 40-95% by weight of an alkanediol having a C3 to C5 carbon chain and a C log P of −0.2 to −1.1,
c) 5-60% by weight of water and
d) one or more additives to adjust the pH of the solution to 3.0 to 6.0 inclusive,
   wherein the total amount of components a) to d) is 100% by weight.

14 Claims, No Drawings

STABLE SOLUTION OF HEXAMIDINE SALTS IN ALKANEDIOL-WATER MIXTURES, WITH ANTIMICROBIAL AND SKIN-MOISTURISING EFFECT

The invention relates to chemically and physically stable solutions of hexamidine salts in a mixture of water and at least one alkanediol. The at least one alkanediol has a straight or branched C3 to C5 carbon chain. The C log P is −0.2 to −1.1. For chemical stabilization, the pH of the solutions according to the invention is adjusted in the range from 3.0 to 6.0. The solutions according to the invention show synergistic antimicrobial and skin-moisturizing effects which exceed the effects of their individual components.

Body care products and cosmetics are commonly used in a non-sterile environment. As water-based mixtures, they provide a good breeding ground for harmful microorganisms. Only the addition of antimicrobial agents ensures adequate preservation of the products, and thus guarantees the safety of consumers. However, many of the preservatives used in personal care products may also exhibit undesirable side effects in addition to their desired protective properties. Thus, the alkyl esters of 4-hydroxybenzoic acid known as "parabens" show a weak hormonal effect. Isothiazolinone derivatives and antimicrobial fragrances such as benzyl alcohol or farnesol, proved to be sensitizing or allergenic. The use of formaldehyde-releasing substances is increasingly considered questionable due to the carcinogenic effect of formaldehyde. Halogen containing preservatives such as chlorphenesin, triclosan or bronopol have also come under criticism because of their toxicity and possible sensitizing properties. Against this background, the effective and safe preservation of personal care products is a challenge for all manufacturers of such articles. This particularly applies to products for people with sensitive or irritated skin, as well as facial and personal care products and products for children.

Hexamidine diisethionate (I) (chemical name: 2-hydroxyethanesulfonic acid-4,4'-[1,6-hexanediylbis(oxy)]dibenzenecarboximidamide, CAS No. 659-40-5 is compared with the preservatives mentioned above a very mild and safe antimicrobial agent with good tolerability and low risk of skin irritation (International Journal of Toxicology 2007, vol. 26, Suppl. 3, Pp. 79-88). Hexamidine diisethionate exhibits a broad antimicrobial spectrum of activity against bacteria, yeasts and fungi. The substance is used inter alia as an antiseptic agent in oral and eye care. However, as a solid hexamidine diisethionate is difficult to handle. In powder form, it can develop dust during handling that irritates the respiratory tract. In water hexamidine salts are only moderately soluble, so they must be dissolved with heating. In addition, the cationic hexamidine can form sparingly soluble salts in solution with anionic components. At high pH, hexamidine is generally poorly soluble in water. All this can complicate the use of hexamidine salts in cosmetic or dermatological products. Moreover, hexamidine diisethionate alone is not sufficiently effective as the sole preservative. It would therefore be desirable to have a stable liquid concentrate of hexamidine in a solvent which enhances its preservative effect while facilitating handling.

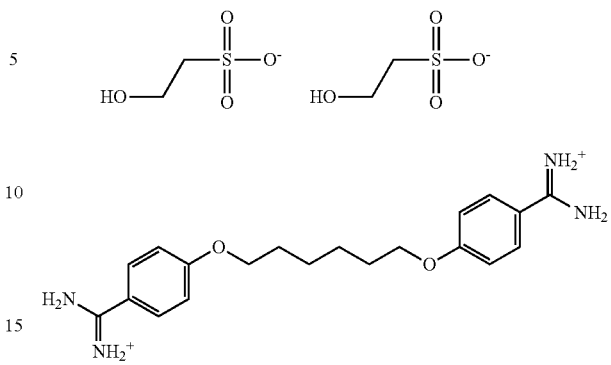

An alternative way of protecting cosmetics from microbiological contamination is the use of alkane polyols having antimicrobial activity. In particular, long-chain C6 to C10 alkanediols such as 1,2-hexanediol, 1,2-octanediol and 1,2-decanediol are used. However, due to their skin-irritating action, their characteristic odor, their low water solubility and their destabilizing effect on emulsions and gels, these substances can only be used in limited concentrations. Furthermore, they produce a greasy skin feel that is not always desirable. In contrast, short-chain diols with C3 to C5 alkyl chains have a higher skin compatibility. These diols are usually odorless, water soluble and largely compatible with O/W emulsions and other galenic forms. In addition, C3 to C5 alkanediols produce a more pleasant and more neutral skin feel than the long chain diols. However, their antimicrobial activity is significantly less pronounced than that of the long-chain diols (see Symrise, DE20221386U1, application date Oct. 17, 2002). For cost-effective preservation of cosmetic products, the short-chain C3 to C5 diols are therefore usually combined with other preservatives. Furthermore, short-chain diols are known as skin care products and moisturizers (see, i.a. Symrise, US20100216892A1, priority Jul. 6, 2007). More hydrophilic C3 polyols, such as 1,2-propanediol or glycerol, are generally used in relatively large amounts for moisturizing the skin. However, they can produce an unpleasantly sticky feeling on the skin. In particular, 1,2-propanediol may also irritate the skin. Therefore, it would be desirable to combine medium-chain alkanediols with preserving substances such as hexamidine diisethionate. Ideally, this combination would enhance both the antimicrobial effect and the skin-care effect.

The literature describes combinations of alkanediols and hexamidine diisethionate:

EP1477157B1 (Procter & Gamble, priority: 16 May 2003) discloses mixtures containing C6 to C9 alkanediols, amidines and water. A stabilizing effect of the C6 to C9 diols on amidines in aqueous solution is disclosed, whereby a dependence of the stabilization on the negative decadic logarithm of the water/n-octanol distribution coefficient C log P (also known as "log KOW") is established. According to the patent, exclusively alkanediols with a C log P value of +0.2 to +1.55 have a stabilizing effect on amidines in aqueous solution. Particularly suitable are C6 to C9 alkanediols such as 1,2-hexanediol (C log P=+0.25), 1,7-heptanediol (C log P=+0.46) or 1,2-octanediol (C log P=+1.32). Furthermore, it is disclosed that more hydrophilic alkanediols with C log P<0.2, as well as more hydrophobic alkanediols with C log P>1.55 have no stabilizing effect on amidines in solution. A suitable pH range for amidines is given as pH 4 to 7.5, preferably pH 5 to 6.5, since pH values above 7.5 lead to a basic hydrolysis of the amidine.

Hexamidine diisethionate (I) is commercially available, inter alia from BASF under the brand name "Elestab HP100". The corresponding data sheet specifies a compatible pH range of 3-8. It is also mentioned that hexamidine diisethionate is soluble in 1,2-propanediol. From the company COBIOSA a solution is available under the brand name COBIOSTAB 400 which is composed of 1,2-propanediol, water and hexamidine diisethionate. A disadvantage of 1,2-propanediol as a solvent is its limited miscibility with lipophilic phases, its low intrinsic antimicrobial activity and the aforementioned skin-irritating action.

The object of the invention is to provide solutions of hexamidine salts in C3 to C5 alkanediols and water that are easy to operate with. The solutions are said to exhibit synergistic antimicrobial and skin moisturizing effects and to be chemically and physically stable over a wide temperature range. According to the invention this object is achieved by a temperature-stable solution consisting of a) 0.1-10% by weight of at least one hexamidine salt,
b) 40-95% by weight of an alkanediol having a C3 to C5 carbon chain and a C log P of −0.2 to −1.1,
c) 5-60% by weight of water
and
d) one or more additives to adjust the pH of the solution to 3.0 to 6.0 inclusive, wherein the total amount of components a) to d) is 100% by weight.

Preferably, the hexamidine salt is a) hexamidine diisethionate.

The at least one alkanediol b) is selected from 1,3-propanediol, 1,2-butanediol, 1,3-butanediol (butylene glycol), 2,3-butanediol, 1,2-pentanediol (pentylene glycol), 1,5-pentanediol and 3-methyl-1,3-butanediol (isopentyldiol), preferably 1,2-pentanediol and 1,3-butanediol, most preferably 1,2-pentanediol.

As expected, short-chain C3 to C5 alkanediols are poor solvents for hexamidine diisethionate (see Table 1, Comparative Examples L-Q). Surprisingly, this also applies to the short-chain 1,3-propanediol (Comparative Example R), while the isomeric 1,2-propanediol is a good solvent for hexamidine diisethionate (Comparative Example S).

Pure water also dissolves hexamidine diisethionate at 20° C. only up to a saturation concentration of 3.5% (Comparative Example T). Surprisingly, it was however found that hexamidine diisethionate in mixtures of water and short-chain C4 to C5 alkanediols or, 3-propanediol is very soluble. This observation is in contrast to the literature. Particularly suitable solvents were combinations of water and alkanediols with a C log P value of −0.2 to −1.1 (see Table 1, Examples A-K). The method used to determine the state of aggregation of the mixtures is described in detail in Example 1.

TABLE 1

Physical properties of mixtures of hexamidines diisethionates, alkanediols and water (− = solid, 0 = two-phase mixture, + = clear liquid)

| | Alkanediol | | | Hexamidine | | Aggregate states of the mixtures at: | | | | | |
|---|---|---|---|---|---|---|---|---|---|---|---|
| # | Substance | ClogP | % | Diisethionate | H₂O | −20° C. | −10° C. | 0° C. | +10° C. | +20° C. | +50° C. |
| A | 1,2-pentanediol | −0.28 | 40% | 5% | 55% | 0 | 0 | + | + | + | + |
| B | 1,2-pentanediol | −0.28 | 70% | 5% | 25% | 0 | + | + | + | + | + |
| C | 1,2-pentanediol | −0.28 | 75% | 5% | 20% | + | + | + | + | + | + |
| D | 1,2-pentanediol | −0.28 | 85% | 5% | 10% | + | + | + | + | + | + |
| E | 1,2-pentanediol | −0.28 | 90% | 5% | 5% | + | + | + | + | + | + |
| F | 3-methyl-1,3-butanediol | −0.34 | 75% | 5% | 20% | + | + | + | + | + | + |
| G | 1,5-pentanediol | −0.60 | 40% | 5% | 55% | 0 | 0 | 0 | + | + | + |
| H | 1,3-butanediol | −0.69 | 75% | 5% | 20% | + | + | + | + | + | + |
| I | 1,2-butanediol | −0.81 | 75% | 5% | 20% | 0 | 0 | + | + | + | + |
| J | 2,3-butanediol | −0.99 | 75% | 5% | 20% | + | + | + | + | + | + |
| K | 1,3-propanediol | −1.04 | 75% | 5% | 20% | + | + | + | + | + | + |
| | Non-inventive comparative examples | | | | | | | | | | |
| L | 1,2-pentanediol | −0.28 | 95% | 5% | 0% | 0 | 0 | 0 | 0 | 0 | + |
| M | 3-methyl-1,3-butanediol | −0.34 | 95% | 5% | 0% | 0 | 0 | 0 | 0 | 0 | 0 |
| N | 1,5-pentanediol | −0.60 | 95% | 5% | 0% | 0 | 0 | 0 | 0 | 0 | 0 |
| O | 1,3-butanediol | −0.69 | 95% | 5% | 0% | 0 | 0 | 0 | 0 | 0 | 0 |
| P | 1,2-butanediol | −0.81 | 95% | 5% | 0% | 0 | 0 | 0 | 0 | 0 | 0 |
| Q | 2,3-butanediol | −0.99 | 95% | 5% | 0% | 0 | 0 | 0 | 0 | 0 | 0 |
| R | 1,3-propanediol | −1.04 | 95% | 5% | 0% | 0 | 0 | 0 | 0 | 0 | 0 |
| S | 1,2-propanediol | −1.34 | 95% | 5% | 0% | 0 | + | + | + | + | + |
| T | — | — | | 5% | 95% | − | − | 0 | 0 | 0 | 0 |

The partition coefficient "P(OW)" refers to the ratio of the concentrations of a substance in equilibrium between the two immiscible liquids n-octanol and water. A common comparison parameter for the phase behavior of a substance is the decadic logarithm of the distribution coefficient log P (OW)=log [c (n-octanol)/c (water)]. This "log P" value is a widely used measure of the hydrophilicity or Lipophilicity of a substance. The value can be determined experimentally as well as calculated. The calculated value is also called "calculated log P" ("C log P"). In the production of multi-phase cosmetics, among other things, the C log P value is useful for predicting the distribution behavior of ingredients between the oil and water phases. High C log P values indicate that the substance in question preferentially migrates into the oil phase, while low and in particular negative C log P values indicate high water solubility.

Prediction of the phase behavior is among other things useful to optimize the activity of an active substance or its transport to its destination. For example, antimicrobial agents are most effective when in the water phase or at the phase boundary to a lipophilic phase. The hexamidine salt solutions of the invention are chemically stable within a pH range between pH 3.0 and 6.0. This is especially true for storage of the solutions at temperatures>20° C. The optimal pH range is thus significantly narrower than described in the literature. The results obtained for the pH dependence of the stability of hexamidine salts are summarized in Table 2. During storage at 42° C., above pH 6.0, rapid hydrolysis of the amidine occurs within a few weeks (Table 2, Solutions J-N). At low pH<3.0, gradual hydrolysis of the amidine is also observed (Table 2, solutions A-C). The pH of hexamidine solutions may vary depending on the counterion and on the method of preparation.

Therefore, the pH of the solutions may need to be adjusted accordingly with the aid of an acid or base or a buffer system.

TABLE 2 pH-dependent stability of hexamidine diisethionate (HX) in solution

| | mass-% | | | | | | Fl. % hexamidine (HPLC, 210 nm) after X weeks storage at 42° C. | | | |
|---|---|---|---|---|---|---|---|---|---|---|
| I of solution | 1,2-pentane-diol | H$_2$O | HX | pH regulator | pH (T0) | pH (10 W) | T0 | 2 W | 4 W | 10 W |
| A | 75% | 20% | 5% | citric acid | 2.8 | 2.9 | 99.7% | 99.1% | 99.0% | 97.1% |
| B | 75% | 20% | 5% | DL-lactic acid | 2.8 | 2.9 | 99.7% | — | 98.8% | 97.2% |
| C | 47.5% | 47.5% | 5% | citric acid | 2.8 | 2.8 | 99.3% | 99.0% | 98.8% | 96.8% |
| D | 47.5% | 47.5% | 5% | — | 4.1 | 4.3 | 99.3% | 99.1% | 99.3% | 99.2% |
| E | 75% | 20% | 5% | — | 4.3 | 4.9 | 99.8% | — | 99.1% | 99.1% |
| F | 47.5% | 47.5% | 5% | NaHCO$_3$ | 5.0 | 4.5 | 99.3% | 99.3% | 99.4% | 99.2% |
| G | 47.5% | 47.5% | 5% | NaHCO$_3$ | 5.5 | 4.9 | 99.3% | 99.3% | 99.2% | 99.2% |
| H | 75% | 20% | 5% | NaHCO$_3$ | 5.8 | 5.8 | 99.3% | 99.3% | 99.3% | 99.3% |
| I | 47.5% | 47.5% | 5% | NaHCO$_3$ | 5.8 | 5.7 | 99.4% | 99.3% | 99.3% | 99.2% |
| J | 47.5% | 47.5% | 5% | NaHCO$_3$ | 6.1 | 8.8 | 99.3% | 99.2% | 96.6% | 65.4% |
| K | 47.5% | 47.5% | 5% | NaHCO$_3$ | 6.5 | 8.7 | 99.3% | 99.2% | 99.1% | 88.3% |
| L | 47.5% | 47.5% | 5% | NaHCO$_3$ | 7.0 | 8.8 | 99.4% | 93.1% | 70.1% | 44.7% |
| M | 47.5% | 47.5% | 5% | NaHCO$_3$ | 7.4 | 8.7 | 99.2% | 85.1% | 64.9% | 41.4% |
| N | 47.5% | 47.5% | 5% | NaHCO$_3$ | 7.7 | 8.8 | 99.3% | 84.3% | 64.0% | 41.2% |

As optional additives for adjusting the pH to 3.0 to 6.0, organic or inorganic bases are selected, preferably alkali and alkaline earth metal oxides, hydroxides, alkoxides, carbonates and bicarbonates or organic or inorganic acids, preferably organic carboxylic acids and sulfonic acids. Particularly preferred are isethionic acid and citric acid. The solutions according to the invention are clear, stable and homogeneous over a wide temperature range. A crystallization of the solid components at low temperature occurs as little as a chemical decomposition of hexamidine at a higher temperature.

Cold and heat-stable liquid mixtures such as the hexamidine solutions according to the invention are advantageous because on the one hand the development of mucous membrane irritant dusts is avoided, which occur when handling solid hexamidine salts. Furthermore, the use of the solutions saves time, energy and production capacity, since liquid mixtures can generally be more easily and accurately dosed, for example by pumping, pouring or sucking. In addition, the incorporation of a liquid into liquid products is faster, more effective, and more uniform than the incorporation of a solid. For example, formation of lumps is avoided.

As expected, the solutions according to the invention have an increased antimicrobial activity compared to the individual components. Table 3 shows by way of example the minimum inhibitory concentrations (MIC) of the solution according to the invention according to Table 1 C in comparison to its individual components. The test procedure is described in Example 2.

TABLE 3

Minimum inhibitory concentrations (MIC) against microorganisms

| | Minimal Inhibitory Concentration (MIC) | | |
|---|---|---|---|
| microorganism | solution according to table 1C (5% hexamidine diisethionate) | hexamidine diisethionate | 1,2-pentanediol |
| Staphylococcus aureus | 0.025% | 0.0025% | 4.0% |
| Pseudomonas aeruginosa | 1.0% | 0.1% | 2.5% |
| Escherichia coli | 0.5% | 0.01% | 2.5% |

TABLE 3-continued

Minimum inhibitory concentrations (MIC) against microorganisms

| | Minimal Inhibitory Concentration (MIC) | | |
|---|---|---|---|
| microorganism | solution according to table 1C (5% hexamidine diisethionate) | hexamidine diisethionate | 1,2-pentanediol |
| Aspergillus brasiliensis | 0.05% | 0.0005% | 2.5% |
| Candida albicans | 0.5% | 0.01% | 2.5% |

Surprisingly, however, it has been found that the solutions according to the invention also show an additional synergistic effect: in comparison with the alkanediol containing they have an increased ability to moisturize the human skin. For example, it has been found that a 2% aqueous solution of the solution according to the invention from Table 1 C has a stronger moisturizing effect when applied to the skin than a 3% aqueous solution of 1,2-pentanediol. This corresponds to at least a doubling of the effectiveness of the humectant 1,2-pentanediol within the solution according to the invention. The data obtained by means of a corneometry measurement are summarized in Table 4. The performance of the test is described in Example 3.

TABLE 4

Corneometry test for moisturizing effect

| test | | corneometry, % change compared to T0 | | | | |
|---|---|---|---|---|---|---|
| substance | concentration | after 1 h | 2 h | 4 h | 8 h | 24 h |
| 1,2-pentanediol | 3% in H$_2$O | +18.8% | +31.6% | +37.7% | +21.6% | +13.1% |
| solution according to table 1C | 2% in H$_2$O (=1.5% 1,2-pentanediol) | +29.6% | +37.2% | +26.1% | +22.0% | +18.5% |
| glycerin | 3% in H$_2$O | +34.3% | +40.2% | +39.5% | +29.9% | +17.5% |
| dist. H$_2$O | 100% | −6.1% | −5.6% | −2.9% | −0.4% | +1.6% |

The solutions according to the invention can be used as broad-spectrum preservatives in cosmetics and personal care products, wherein the concentration of hexamidine in the end product does not exceed 0.1% by weight. The solutions according to the invention are able to kill various microorganisms. Generally, the term "microorganism" includes bacteria and fungi, especially Gram-positive and Gram-negative bacteria, as well as yeasts and molds. Examples of target organisms (without excluding character) are: *Escherichia coli, Staphylococcus aureus, Enterococcus hirae, Pseudomonas aeruginosa, Burkholderia cepacia, Candida albicans* and/or *Aspergillus brasiliensis*.

As the at least one hexamidine salt a) salts of hexamidine are used, which are suitable for cosmetic or dermatological applications. Salts of hexamidine with carboxylic acids and/or sulfonic acids and/or phenols are preferred. Hexamidine is particularly preferably used as the salt of isethionic acid.

The alkanediol component used is at least one alkanediol b) whose decadic logarithm of the n-octanol-water partition coefficient (C log P) is between −0.2 and −1.1. Preferably, the at least one alkanediol b) is a C 3 to C 5 alkanediol, preferably a C 4 to C 5 alkanediol, more preferably 1,2-pentanediol. The at least one alkanediol b) contained in the product may have additional functions within the finished product, e.g. as a humectant, as penetration-promoting reagent or as an agent for influencing the skin feel.

To stabilize the solutions according to the invention, water c) is used in a concentration of 5 to 60% by weight, preferably in a concentration of 5 to 30% by weight.

Regardless of their antimicrobial and skin-moisturizing properties, the components contained in the solutions according to the invention can also fulfill other tasks. Examples of non-exclusive character are applications as conditioner, skin lightener, exfoliant, enzyme inhibitor, antioxidant, light and UV protection, to regulate sebum production, to influence rheology and viscosity, as well as to positively affect age-related and/or environmental skin or hair changes.

Using the solution according to the invention, it is also possible to produce a product, in particular a cosmetic and/or pharmaceutical and/or dermatological and/or hygienic product, containing a solution as explained above. In other words, the solution according to the invention is used for the preservation of cosmetic and/or pharmaceutical and/or dermatological and/or hygienic products, in particular cosmetic and dermatological products, in particular for the growth inhibition or killing of microorganisms.

A further use of the solution according to the invention is achieved in the case of products to which the solution according to the invention is added for the purpose of moisturizing the skin. As "hygienic preparation" or "hygienic product" in particular household or cleaning products, as well as fragrance preparations are understood.

The addition of the solutions according to the invention to the cosmetic and/or pharmaceutical and/or dermatological and/or hygienic product can take place at any time during production, for example during the production of an aqueous phase or at the end of the production process.

Also included within the scope of the invention is a method for growth inhibition or killing of microorganisms in which the solutions of the invention are added to products from the fields of cosmetics, dermatology, personal care and personal hygiene. Further scope of the invention is a method for moisturizing the skin, in which the solutions according to the invention find application for this purpose.

The solution according to the invention is also used in a product, in particular a cosmetic or dermatological product, containing the solution according to the invention, wherein the product contains 0.1 to 2.0% by weight alkanediol(s) and 0.01 to 0.1% by weight amidine(s).

The respective product can be present in any form, in particular as:
  a. solution,
  b. suspension,
  c. emulsion,
  d. gel,
  e. ointment,
  f. paste,
  g. powder,
  h. in pieces or as a block of solid,
  i. foam,
  j. formulation system based on microencapsulation, liposomes or similar microscopic structures,
  k. combinations of forms a-j

EXAMPLES/EXPERIMENTAL PART

Example 1—Physical Stability of the Solutions According to the Invention

Hexamidine diisethionate is dissolved at 50° C. in various alkanediols, optionally with the addition of water. The solutions are kept at −20° C. for 16-20 h. The mixtures are then heated to +20° C. in 2° C. increments over 10 h. The mixtures are then cooled back to −20° C. within 10 h in 2° C. increments. The observed states of aggregation of the mixtures are summarized in Table 1 (−=solid, 0=two-phase mixture, +=clear liquid).

Example 2—Determination of Minimum Inhibitory Concentration

Minimal inhibitory concentrations against bacteria, fungi and yeasts were determined by means of a suspension test.

For this purpose, nine-stage dilution series of the respective test substances were prepared in 1:1 mixtures of CASO broth and distilled water. For the tests with mushrooms and yeasts in each case 2% dextrose was added. Each microorganism was tested separately in a test tube containing 10 ml of said culture medium. To each tube was added 0.1 ml of a suspension containing $5\times10^8$ colony forming units (CFU) for bacteria and $1\times10^7$ CFU for fungi and yeasts, respectively. Each tube was incubated for 3 days at 37° C. (bacteria) or for 4 days at 30° C. (fungi and yeasts). The minimum inhibitory concentration was defined as the concentration at which no turbidity or other visible signs of microbial growth were observed after the end of the test period. The results obtained are shown in Table 3.

Example 3—Determination of the Moisturizing Effect by Means of Corneometry

To test the moisturizing effect of various substances and mixtures, the test substances were diluted with distilled water to a concentration of 2-3%. The diluted solutions were applied to the forearms of healthy volunteers (number: 12, age: 19-64 years). Before and after the simple application, the skin moisture of the treated skin areas was measured instrumentally with the aid of a Corneometer CM825, combined with a Cutometer dual MPA 580 from Courage & Khazaka. All measurements were preceded by acclimatization of the subjects in a controlled environment (21° C.±1° C., 45%±10% humidity). The measurement results are given as a percentage change from the initial value after 1 h, 2 h, 4 h, 8 h and 24 h and are summarized in Table 4.

Example 4—Shower Gel Preserved with Inventive Solution According to Table 1 C

| phase | ingredient | INCI name | % |
|---|---|---|---|
| A | water | Aqua | 72.4 |
|  | xanthan gum | Xanthan gum | 0.6 |
|  | Plantacare 818UP | Cocoglucoside | 15.0 |
|  | Plantapon ACG HC | Sodium cocoamphoacetate | 5.0 |
|  | Tegobetain F50 | Cocamidopropyl betain | 5.0 |
| B | citric acid (50% aqueous solution) | Citric acid (and) Aqua | pH 5.5 |
| C | Inventive solution according to table 1C | pentylene glycol (and) water (and) hexamidine diisethionate | 2.0 |

Xanthan gum and water are stirred at 700-800 rpm until complete hydration of the gelling agent. The remaining Phase A components are added at 400 rpm in the order listed. The pH of the mixture is lowered to 5.5 as needed. Subsequently, the solution according to the invention is added with stirring.

Comparative Example 5—Shower Gel, Preserved with Hexamidine Diisethionate

| phase | ingredient | INCI name | % |
|---|---|---|---|
| A | water | Aqua | 62.4 |
|  | Xanthan gum | Xanthan gum | 0.6 |
|  | Plantacare 818UP | Cocoglucoside | 15.0 |
|  | Plantapon ACG HC | Sodium cocoamphoacetate | 5.0 |
|  | Tegobetain F50 | Cocamidopropyl betain | 5.0 |
| B | citric acid (50% water solution) | Citric acid (and) Aqua | pH 5.5 |
| C | water | Aqua | 10.0 |
|  | MinaSolve Hexam | Hexamidine Diisethionate | 0.1 |

Xanthan gum and water are stirred at 700-800 rpm until complete hydration of the gelling agent. The remaining Phase A components are added at 400 rpm in the order listed. The pH of the mixture is lowered to 5.5 as needed. Subsequently, hexamidine diisethionate is dissolved in water and the resulting aqueous solution is added with stirring.

Comparative Example 6—Shower Gel Preserved with Pentylene Glycol

| phase | ingredient | INCI name | % |
|---|---|---|---|
| A | water | Aqua | 71.4 |
|  | xanthan gum | Xanthan gum | 0.6 |
|  | Plantacare 818UP | Cocoglucoside | 15.0 |
|  | Plantapon ACG HC | Sodium cocoamphoacetate | 5.0 |
|  | Tegobetain F50 | Cocamidopropyl betain | 5.0 |
| B | citric acid (50% water solution) | Citric acid (and) Aqua | pH 5.5 |
| C | MinaCare Pentiol Green+ | Pentylene Glycol | 3.0 |

Xanthan gum and water are stirred at 700-800 rpm until complete hydration of the gelling agent. The remaining Phase A components are added at 400 rpm in the order listed. The pH of the mixture is lowered to 5.5 as needed. Subsequently, pentylene glycol is added with stirring.

Example 7—O/W Cream Preserved with Inventive Solution According to Table 1 C

| phase | ingredient | INCI name | % |
|---|---|---|---|
| A | water | Aqua | 84.4 |
|  | inventive solution according to table 1C | Pentylene glycol (and) Water (and) hexamidine diisethionate | 1.0 |
|  | xanthan gum | Xanthan gum | 0.5 |
| B | Emulgade PL 68/50 | Cetearyl Glucoside (and) Cetearyl Alcohol | 5.0 |
|  | Lipex Shea | *Butyrospermum Parkii* (Shea) Butter | 3.0 |
|  | Jojobaöl | *Simmondsia Chinensis* (Jojoba) Seed Oil | 3.0 |
|  | Haselnussöl | *Corylus Avellana* (Hazelnut) Seed Oil | 3.0 |
| C | Bioxan T70 | Tocopherol | 0.1 |
| D | citric acid (50% wässr. Lsg.) | Citric acid (and) Aqua | pH 5.5 |

The solution according to the invention according to Table 1C is mixed by stirring with water, whereby a clear solution is formed. Xanthan gum is added and stirred at 700-800 rpm until complete hydration of the gelling agent with a dispersing stirrer. Subsequently, phase A is heated with stirring to 75-80° C. The components of phase B are heated together to 80° C. and thereby melted. Phase B is added to hot phase A at 75-80° C. The mixture is mixed for 3 minutes at 10,000 rpm using Ultra-Turrax. The emulsion is then stirred for 30 minutes at 1000 rpm using a dispersing stirrer and at 700 rpm until reaching 20-25° C. At <40° C. tocopherol is added with stirring. Finally, the pH of the mixture is lowered to 5.5 as needed.

Comparative Example 8—O/W Cream Preserved with Hexamidine Diisethionate

| phase | ingredient | INCI name | % |
|---|---|---|---|
| A | water | Aqua | 85.3 |
|   | MinaSolve Hexam | hexamidine diisethionate | 0.1 |
|   | xanthan gum | Xanthan gum | 0.5 |
| B | Emulgade PL 68/50 | Cetearyl Glucoside (and) Cetearyl Alcohol | 5.0 |
|   | Lipex shea | Butyrospermum Parkii (Shea) Butter | 3.0 |
|   | jojoba oil | Simmondsia Chinensis (Jojoba) Seed Oil | 3.0 |
|   | hazelnut oil | Corylus Avellana (Hazelnut) Seed Oil | 3.0 |
| C | Bioxan T70 | Tocopherol | 0.1 |
| D | citric acid (50% water solution) | Citric acid (and) Aqua | pH 5.5 |

Hexamidine diisethionate is dissolved in water with stirring. Xanthan gum is added and stirred at 700-800 rpm until complete hydration of the gelling agent with a dispersing stirrer. Subsequently, phase A is heated with stirring to 75-80° C. The components of phase B are heated together to 80° C. and thereby melted. Phase B is added to hot phase A at 75-80° C. The mixture is mixed for 3 minutes at 10,000 rpm using Ultra-Turrax. The emulsion is then stirred for 30 minutes at 1000 rpm using a dispersing stirrer and at 700 rpm until reaching 20-25° C. At <40° C. tocopherol is added with stirring. Finally, the pH of the mixture is lowered to 5.5 as needed.

Comparative Example 9—O/W Cream Preserved with Pentylene Glycol

| phase | ingredient | INCI name | % |
|---|---|---|---|
| A | water | Aqua | 82.4 |
|   | MinaCare Pentiol Green+ | Pentylene Glycol | 3.0 |
|   | xanthan gum | Xanthan gum | 0.5 |
| B | Emulgade PL 68/50 | Cetearyl Glucoside (and) Cetearyl Alcohol | 5.0 |
|   | Lipex shea | Butyrospermum Parkii (Shea) Butter | 3.0 |
|   | jojoba oil | Simmondsia Chinensis (Jojoba) Seed Oil | 3.0 |
|   | hazelnut oil | Corylus Avellana (Hazelnut) Seed Oil | 3.0 |
| C | Bioxan T70 | Tocopherol | 0.1 |
| D | citric acid (50% water solution) | Citric acid (and) Aqua | pH 5.5 |

Pentylene glycol is dissolved in water with stirring. Xanthan gum is added and stirred at 700-800 rpm until complete hydration of the gelling agent with a dispersing stirrer. Subsequently, phase A is heated with stirring to 75-80° C. The components of phase B are heated together to 80° C. and thereby melted. Phase B is added to hot phase A at 75-80° C. The mixture is mixed for 3 minutes at 10,000 rpm using Ultra-Turrax. The emulsion is then stirred for 30 minutes at 1000 rpm using a dispersing stirrer and at 700 rpm until reaching 20-25° C. At <40° C. tocopherol is added with stirring. Finally, the pH of the mixture is lowered to 5.5 as needed.

Example 10—Microbiological Preservative Load Tests According to ISO 11930

In order to verify the sufficient antimicrobial preservation of the personal care products produced in the preceding examples and comparative examples, the products were each subjected to a microbiological preservative loading test. The test consists of the contamination of the test product with an inoculum of five different types of microorganisms specified by ISO 11930, the removal of samples from the test product after 7, 14 and 28 days and the determination of the number of test microbes in the samples taken. The preservative properties are sufficient if, under the conditions of the test, there is a clear reduction or, if necessary, no increase in the number of germs in the inoculated test product after the prescribed times. The acceptance criteria according to ISO 11930 are summarized in Table 5. The values given correspond in each case to the decadic logarithm of the change in the number of colony-forming units per gram (Δ CFU/g).

Positive numbers represent a reduction in the number of bacteria, negative numbers an increase. The changes in the germ load of the tested products are recorded in Tables 6 and 7.

TABLE 5

| Acceptance criteria "A" for adequate preservation according to ISO 11930 | | | |
|---|---|---|---|
| | Minimum required Δ log (CFU/g) according to ISO 11930 (NI = no increase, no higher germ load than the pre-value) | | |
| test germ | T7 | T14 | T28 |
| Aspergillus brasiliensis | — | ≥0 + NI | ≥1 + NI |
| Candida albicans | ≥1 | ≥1 + NI | ≥1 + NI |
| Pseudomonas aeruginosa | ≥3 | ≥3 + NI | ≥3 + NI |
| Staphylococcus aureus | ≥3 | ≥3 + NI | ≥3 + NI |
| Escherichia coli | ≥3 | ≥3 + NI | ≥3 + NI |

TABLE 6

Preservative load tests of shower gels

| | Shower gel according to example 4, preserved with 2.0% of the solution Table 1C (0.1% hexamidine and 1.5% pentylene glycol) [Δ log (CFU/g)] | | | Shower gel after Comparative Example 5, preserved with 0.1% hexamidine diisethionate [Δ log(CFU/g)] | | | Shower gel after Comparative Example 6, preserved with 3.0% pentylene glycol [Δ log(CFU/g)] | | |
|---|---|---|---|---|---|---|---|---|---|
| test germ | T7 | T14 | T28 | T7 | T14 | T28 | T7 | T14 | T28 |
| *Aspergillus brasiliensis* | — | >2.6 | >2.6 | — | >2.6 | >2.6 | — | 0.6 | 0.3 |
| *Candida albicans* | >3.3 | >3.3 | >3.3 | 2.9 | >3.3 | >3.3 | 2.5 | >2.9 | >2.9 |
| *Pseudomonas aeruginosa* | >4.8 | >4.8 | >4.8 | 1.7 | 0.6 | 0.0 | >4.2 | >4.2 | >4.2 |
| *Staphylococcus aureus* | >4.5 | >4.5 | >4.5 | 2.1 | 4.5 | −0.7 | 4.5 | >4.5 | >4.5 |
| *Escherichia coli* | >4.7 | >4.7 | >4.7 | 1.5 | 1.1 | >4.7 | >4.4 | >4.4 | >4.4 |

The shower gel preserved with 2% of the inventive solution according to Table 1C (Example 4) meets the A criteria for adequate preservation of cosmetic products according to ISO 1 1930, while with 0.1% hexamidine diisethionate (Comparative Example 5) or 3.0% Pentylene Glycol (Comparative Example 6) did not fully meet the criteria. The deviations from the standard are highlighted in bold.

TABLE 7

Preservative loading tests of O/W emulsions

| | emulsion according to example 7, preserved with 1.0% of the solution Table 1C (0.05% hexamidine and 0.75% pentylene glycol) [Δ log (CFU/g)] | | | emulsion according to comparative example 8, preserved with 0.1% hexamidine diisethionate [Δ log (CFU/g)] | | | emulsion according to comparative example 9, preserved with 3.0% pentylene glycol [Δ log (CFU/g)] | | |
|---|---|---|---|---|---|---|---|---|---|
| test germ | T7 | T14 | T28 | T7 | T14 | T28 | T7 | T14 | T28 |
| *Aspergillus brasiliensis* | — | >2.6 | >2.6 | — | >2.6 | >2.6 | — | 0.3 | 0.1 |
| *Candida albicans* | >3.3 | >3.3 | >3.3 | >3.3 | >3.3 | >3.3 | 3.2 | >4.9 | >4.9 |
| *Pseudomonas aeruginosa* | >4.8 | >4.8 | >4.8 | >4.8 | >4.8 | >4.8 | >4.6 | >4.6 | >4.6 |
| *Staphylococcus aureus* | >4.5 | >4.5 | >4.5 | >4.5 | >4.5 | >4.5 | 1.1 | 2.6 | >4.8 |
| *Escherichia coli* | >4.7 | >4.7 | >4.7 | >4.7 | >4.7 | >4.7 | 1.6 | >4.8 | >4.8 |

The O/W emulsion preserved with 1.0% of the solution according to the invention according to Table 1 C fulfills the A criteria for sufficient preservation of cosmetic products according to ISO 1 1930. To achieve the same antimicrobial effect, twice the amount of 0.1% of the individual substance hexamidine diisethionate is required (Comparative Example 8). In comparison, even 3.0% of pentylene glycol (Comparative Example 9) is not sufficient for complete preservation according to ISO 1 1930. The deviations from the standard are highlighted in bold.

The invention claimed is:

1. A temperature-stable solution comprising:
    a) 0.1-10% by weight of at least one hexamidine salt;
    b) 40-95% by weight of an alkanediol having a C3 to C5 carbon chain and a C log P of −0.2 to 1.1;
    c) 5-60% by weight of water; and
    d) one or more additives for adjusting the pH of the solution from 3.0 to 6.0 inclusive,
    wherein the total amount of components a) to d) is 100% by weight.

2. The temperature-stable solution according to claim 1, wherein the at least one hexamidine salt comprises hexamidine diisethionate.

3. The temperature stable solution according to claim 1, wherein the alkanediol is selected from the group consisting of 1,3-propanediol, 1,2-butanediol, 1,3-butanediol (butylene glycol), 2,3-butanediol, 1,2-pentanediol (pentylene glycol), 1,5-pentanediol and 3-methyl-1,3-butanediol (isopentyldiol).

4. The temperature-stable solution according to claim 1, wherein the additives are selected from the group consisting of organic and inorganic bases.

5. The temperature-stable solution according to claim 1, wherein the additives are selected from the group consisting of organic and inorganic acids.

6. A method for preservation of cosmetics, dermatological products, personal care products or personal hygiene products, comprising adding the temperature-stable solution according to claim 1 to the cosmetics, dermatological products, personal care products or personal hygiene products.

7. The method of claim 6, wherein the preservation comprises inhibition of growth or killing of microorganisms in the cosmetics, dermatology, personal care and personal hygiene products.

8. A method for moistening skin of mammals, comprising applying the temperature-stable solution according to claim 1 to the skin of mammals.

9. A cosmetic or a dermatological product comprising the temperature-stable solution according to claim 1.

10. The temperature stable solution according to claim 1, wherein the alkanediol is selected from the group consisting of 1,2-pentanediol and 1,3-butanediol.

11. The temperature stable solution according to claim 1, wherein the alkanediol is 1,2-pentanediol.

12. The temperature-stable solution according to claim 1, wherein the additives are selected from the group consisting of oxides of alkali metals, oxides of alkaline earth metals, hydroxides, alkoxides, carbonates, and hydrogen carbonates.

13. The temperature-stable solution according to claim 1, wherein the additives are selected from the group consisting of organic carboxylic acids and sulfonic acids.

14. The temperature-stable solution according to claim 1, wherein the additives are selected from the group consisting of isethionic acid and citric acid.

\* \* \* \* \*